United States Patent [19]

Lyons

[11] 3,960,914

[45] June 1, 1976

[54] CONVERSION OF FORMAMIDES TO ISOCYANATES

[75] Inventor: James E. Lyons, Wallingford, Pa.

[73] Assignee: Sun Ventures, Inc., St. Davids, Pa.

[22] Filed: May 6, 1975

[21] Appl. No.: 575,096

[52] U.S. Cl. ............................................. 260/453 P
[51] Int. Cl.² ..................................... C07C 118/04
[58] Field of Search ................................ 260/453 P

[56] References Cited
UNITED STATES PATENTS 3,099,673  7/1963  Kühle .................................. 260/453

*Primary Examiner*—Lewis Gotts
*Assistant Examiner*—Dolph H. Torrence
*Attorney, Agent, or Firm*—J. Edward Hess; Donald R. Johnson; Stanford M. Back

[57] ABSTRACT

Formamides of formula R—NHCHO where R is a lower alkyl, cycloalkyl, aryl or aralkyl can be converted to isocyanates of the formula R—N=C=O when contacted with certain ruthenium, palladium, or platinum dehydrogenation catalysts.

6 Claims, No Drawings

CONVERSION OF FORMAMIDES TO ISOCYANATES

BACKGROUND OF THE INVENTION

This invention relates to the preparation of isocyanates, which are useful intermediates in the preparation of polyurethanes. More particularly, this invention is directed to a process for the conversion of certain defined aliphatic or aryl amides to the corresponding isocyanates, using ruthenium, palladium, platinum catalysts.

Isocyanates are valuable commercial intermediates in the manufacture of polyurethanes as well as in the synthesis of herbicides and pharmaceuticals. They are usually prepared from nitroaromatics in several steps which require relatively expensive reagents. In accordance with the present invention, however, this conversion can be achieved in one inexpensive step from the respective nitrile.

SUMMARY OF THE INVENTION

Thus, in accordance with the present invention, formamides of the formula

R—NHCHO wherein R is lower alkyl, cycloalkyl, aryl, or aralkyl, can be converted to their corresponding isocyanates having the formula

R—N=C=O wherein R is as defined above, by contacting said amides with a dehydrogenation catalyst selected from the group consisting of ruthenium black, platinum black, palladium black, or any one of ruthenium, platinum, or palladium on a suitable support such as carbon, alumina, kieselguhr, corhart, or the like.

DESCRIPTION OF THE INVENTION

The process is conveniently carried out by contacting the desired formamide with the dehydrogenation catalyst at temperatures of from about 50° to 300°C., and preferably at about 75° to 200°C. The reaction may be carried out neat or in the presence of an inert solvent such as benzene, toluene, xylene or the like, i.e. a non-protic solvent. The only essential condition is that the reaction be carried out under substantially anhydrous conditions, although it is preferred that the reaction be carried out under an inert atmosphere such as nitrogen.

The ratio of starting material to catalyst is desirably in the range from about 1:1 to 100:1 by weight, preferably 2:1.

The formamide starting materials, as aforestated, are those compounds having the formula

R—NHCHO where R is as defined above. Illustrative only, and not intended to be all-inclusive, of these compounds, and their corresponding products, are the following amides:

 —NHCHO ⟶ 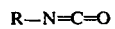 —NCO formanilide      phenylisocyanate

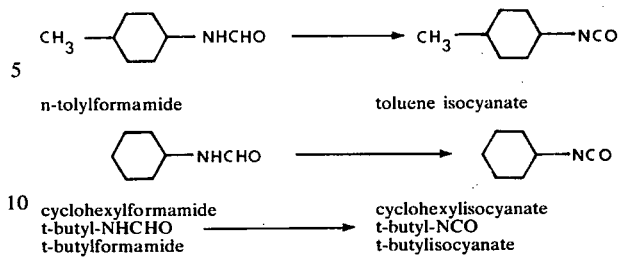

n-tolylformamide      toluene isocyanate

 —NHCHO ⟶  —NCO cyclohexylformamide      cyclohexylisocyanate
t-butyl-NHCHO ⟶ t-butyl-NCO
t-butylformamide      t-butylisocyanate The product is conveniently recovered by simply separating it from the catalyst, which is reusable, and, if desired, evaporating the solution to dryness, or else just leaving it in solution.

The invention will now be illustrated by the following examples.

EXAMPLE 1

2.0 grams of formanilide in 10 ml benzene was refluxed (80°C) for 3.5 hours in the presence of 1.0 gram of palladium black. After filtration of the hot reaction mixture, the solution was analyzed by gas chromatography. Analysis showed that the conversion of formanilide was ~10 percent and the selectivity to phenylisocyanate was 30 percent. The product was identified by comparison of its retention time with pure phenylisocyanate on two different silicone gc columns. The only other by products which were identified were diphenyl urea and benzaldehyde, although a number of unidentified materials were also formed.

EXAMPLE 2

1.0 gram of formanilide in 6 ml of toluene was stirred at 125°C for 4 hours in the presence of 0.50 gram of palladium black. After filtration of the hot reaction mixture, gas chromatographic analysis indicated that phenylisocyanate had been formed.

The invention claimed is:

1. A process for the preparation of isocyanate which comprises contacting an amide of the formula

R—NHCHO wherein R is lower alkyl, cycloalkyl, aryl or aralkyl, with a dehydrogenation catalyst selected from the group consisting of palladium black, palladium on suitable supports, ruthenium black, ruthenium on suitable supports, platinum black, and platinum on suitable supports, at a temperature of from about 50°–300°C, under substantially anhydrous conditions, to form the corresponding isocyanate of the formula

R—N=C=O wherein R is as defined above.

2. The process according to claim 1 wherein the ratio of formamide to catalyst is in the range of from about 1:1 to 100:1 by weight.

3. The process according to claim 2 wherein said ratio is about 2:1 by weight.

4. The process according to claim 1 wherein the temperature is from about 75° to 200°C.

5. The process according to claim 1 wherein the raction is carried out in the presence of a solvent which is inert to the conditions of the reaction.

6. The process according to claim 1 wherein the catalyst is palladium black or palladium on carbon.

* * * * *